United States Patent [19]
Goetz et al.

[11] Patent Number: 5,095,003
[45] Date of Patent: Mar. 10, 1992

[54] OXYTOCIN AND VASOPRESSIN ANTAGONISTS

[75] Inventors: Michael A. Goetz, Fanwood; Lawrence R. Koupal, Colonia; Cheryl D. Schwartz, Westfield; Jerrold M. Liesch, Princeton Junction; Otto D. Hensens, Red Bank, all of N.J.; Paul S. Anderson, Lansdale, Pa.; Roger Freidinger, Hatfield, Pa.; Douglas J. Pettibone, Chalfont, Pa.

[73] Assignee: Merck & Co., Inc., Rahway, N.J.

[21] Appl. No.: 604,394

[22] Filed: Oct. 23, 1990

Related U.S. Application Data

[63] Continuation of Ser. No. 79,573, Aug. 3, 1987, abandoned, which is a continuation-in-part of Ser. No. 896,036, Aug. 13, 1986, abandoned.

[51] Int. Cl.$^5$ .......................... A61K 37/34; C07K 7/16
[52] U.S. Cl. .......................... 514/9; 530/315; 530/317; 530/333; 514/807; 435/7.8; 435/7.1; 435/71.1; 435/7.4; 435/7.6; 436/501
[58] Field of Search ............ 514/9, 807; 530/315, 530/317, 333; 435/7.8, 7.4, 7.6, 7.1, 71.1; 436/501

[56] References Cited

U.S. PATENT DOCUMENTS
4,760,052  7/1988  Callahan et al. .................... 530/315

FOREIGN PATENT DOCUMENTS
1157912  7/1969  United Kingdom ................ 530/317

OTHER PUBLICATIONS

Molecular and Cellular Endocrinology, 22(1981), pp. 117–134, Sawyer et al.
Chem. Abs. vol. 111, No. 11, 90588k, Pettibone et al., 1989 (Endocrinology).
Chem. Abs. 109, No. 9, 72049q, Goetz et al.
Federation Proceedings 43: 87–90 (1984) Sawyer & Manning.
J. Med. Chem. 28: 1759–1760 (1985) Huffman, Ali & Bryan.
Federation Proceedings 45: 205 (1986), Straub, Landvatter & Garvey.
Federation Proceedings 45: 649 (1986), Kinger, Mann, Woodward, Depalma & Brennan.
J. Chem. Soc. (c), p. 526 (1971), Hassall et al.
J. C. S. Chem. Comm. p. 635 (1977), Hassall et al.
Tetrahedron Letters, 49, pp. 4255–4258 (1969), Hammill et al.

Primary Examiner—John Doll
Assistant Examiner—T. Wessendorf
Attorney, Agent, or Firm—Frank P. Grassler; Richard S. Parr; Hesna J. Pfeiffer.

[57] ABSTRACT

Cyclic peptides are produced by the controlled aerobic fermentation of Streptomyces silvensis, ATTCC No. 53525 or ATCC No. 53526. These compounds are antagonists of oxytocin and are useful in the treatment of preterm labor and vasopressin and are thus useful in the treatment and prevention of disease states wherein vasopressin may be involved, for example congestive heart failure, hypertension, edema and hyponatremia.

3 Claims, 8 Drawing Sheets

OXYTOCIN AND VASOPRESSIN ANTAGONISTS

This is a continuation of application Ser. No. 079,573, filed Aug. 3, 1987, now abandoned, which is a continuation-in-part of U.S. Ser. No. 896,036, filed Aug. 13, 1986, now abandoned.

BACKGROUND OF THE INVENTION

This invention pertains to the field of oxytocin and vasopressin antagonists.

In the field of obstetrics, one of the most important problems is the management of preterm labor. A significant number of the pregnancies progressing past 20 weeks of gestation experience premature labor and delivery which is a leading cause of neonatal morbidity and mortality.

It has recently been proposed that a selective oxytocin antagonist would be the ideal tocolytic agent. In the last few years, evidence has accumulated to strongly suggest that oxytocin is the physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part by a well documented increase in the number of oxytocin receptors in this tissue. This 'up-regulation' of oxytocin receptors and enhanced uterine sensitivity appears to be due to trophic effects of rising plasma levels of estrogen towards term. By blocking both the direct (contractile) and indirect (enhanced prostaglandin synthesis) effects of oxytocin on the uterus, a selective oxytocin antagonist would likely be more efficacious for treating preterm labor than current regimens. In addition, since oxytocin at term has major effects only on the uterus, such a compound would be expected to have few, if any, side effects.

Vasopressin (also known as Antidiuretic Hormone, ADH) is a pituitary peptide hormone that is vital for the maintenance of proper water balance in animals and man. The antidiuretic effect of vasopressin concentrates the urine by increasing the reabsorption of water from the kidney filtrate. Thus, even under mild conditions of dehydration enhanced blood levels of vasopressin act to conserve water and control the proper osmolarity of the blood and extracellular fluids. Vasopressin also acts to contract vascular smooth muscle and may normally be involved in the maintenance of peripheral vascular resistance (McNeil, J. R., *Can. J. Physiol Pharmacol* 61: 1226-1235 (1983); Cowley, A. W., Quillen, E. W., and Skelton, M. M., Federation Proceedings 42: 3170-3176 (1983)).

Recent studies have led to the development of relatively potent and specific antagonists of the antidiuretic or pressor effects of vasopressin (Sawyer, W. H.; and Manning, M., *Federation Proceedings* 43: 87-90 (1984)). Because of the prominent actions of vasopressin on renal and cardiovascular function, vasopressin antagonists are useful in the treatment of several conditions including congestive heart failure, hypertension, and states of edema. The salt-sparing, 'water diuretic' activity of vasopressin antagonists would be particularly useful in the treatment of hyponatremia which can arise from a variety of conditions (Zerbe, R., Stropes, L., Robertson, G., *Ann. Rev. Med.* 31: 315-327 (1980)). The currently known vasopressin antagonists are peptide analogues of vasopressin (Huffman, W. H., Ali, F. E., Bryan, W. M. et al. J. *Med Chem* 28: 1759-1760 (1985)) and are, therefore, likely to be rapidly metabolized in vivo and to have little, if any, oral activity (Lynn, R. K., Straub, K. M., Landvatter, S. W., and Garvey, C. T., *Federation Proceedings* 45: 205 (1986); Kinter, L. B., Mann, W. A., Woodward, P., DePalma, D. and Brennan, F., *Federation Proceedings* 45: 649 (1986)).

It is, therefore, an object of the present invention to provide cyclic peptides and synthetic analogues which are antagonists of oxytocin and vasopressin and are useful as pharmaceutical agents. It is also an object of the present invention to provide processes for producing these cyclic peptides. It is a further object of the invention to provide a mixture of cyclic peptides of Formula I and its minor related components A, B, C, D, E, F and G produced by aerobic fermentation of the organism *Streptomyces silvensis*. Another object is to provide cultures of the organism *Streptomyces silvensis* ATCC No. 53525 or ATCC No. 53526 which are capable of producing the cyclic peptides and mixtures thereof. A still further object is to provide synthetic analogues of these cyclic peptides.

SUMMARY OF THE INVENTION

Figure 1:
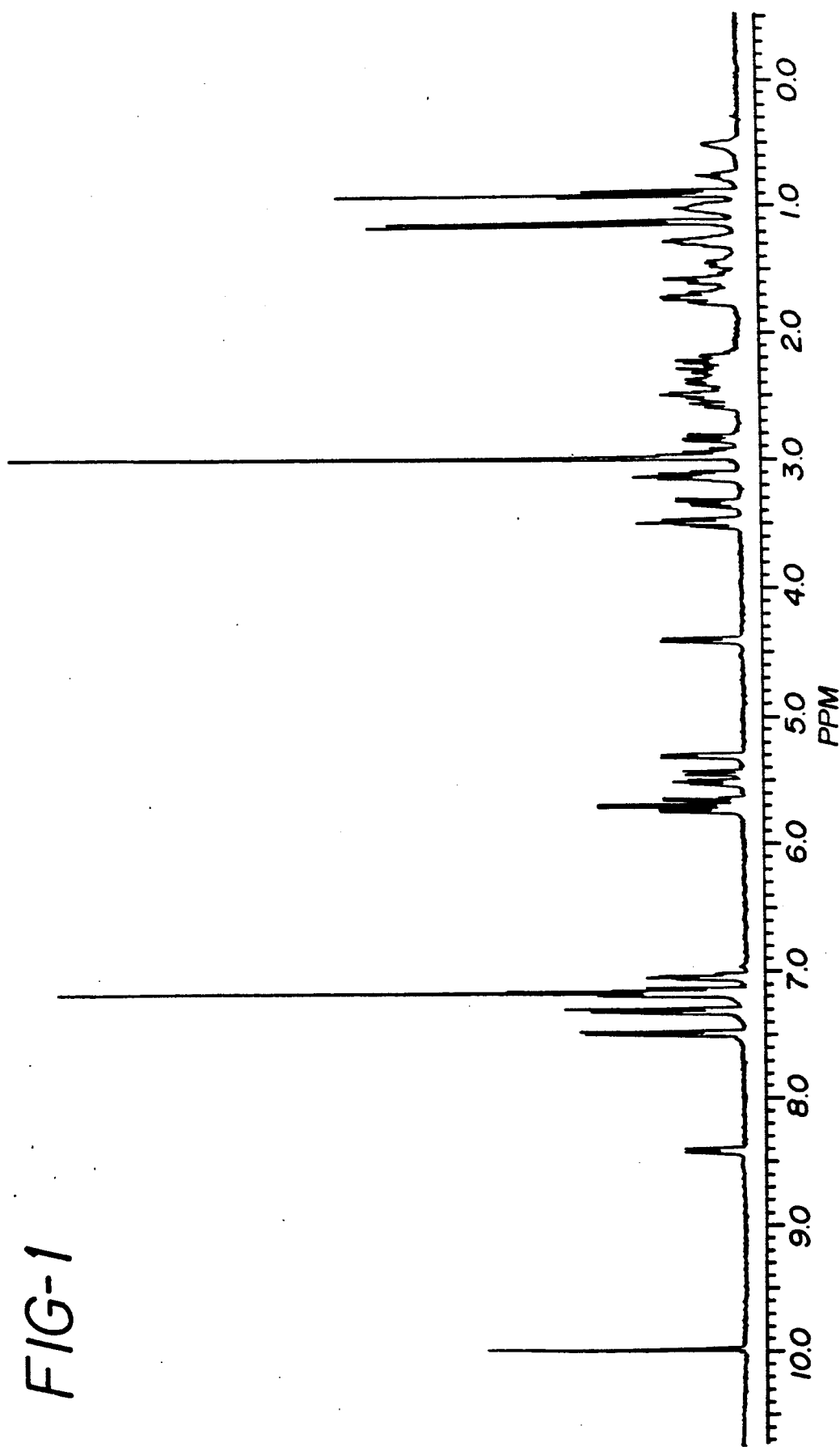
FIG. 1 is a proton nuclear magnetic resonance ($^1$H-NMR) spectrum of the compound of Formula I.
Figure 2:
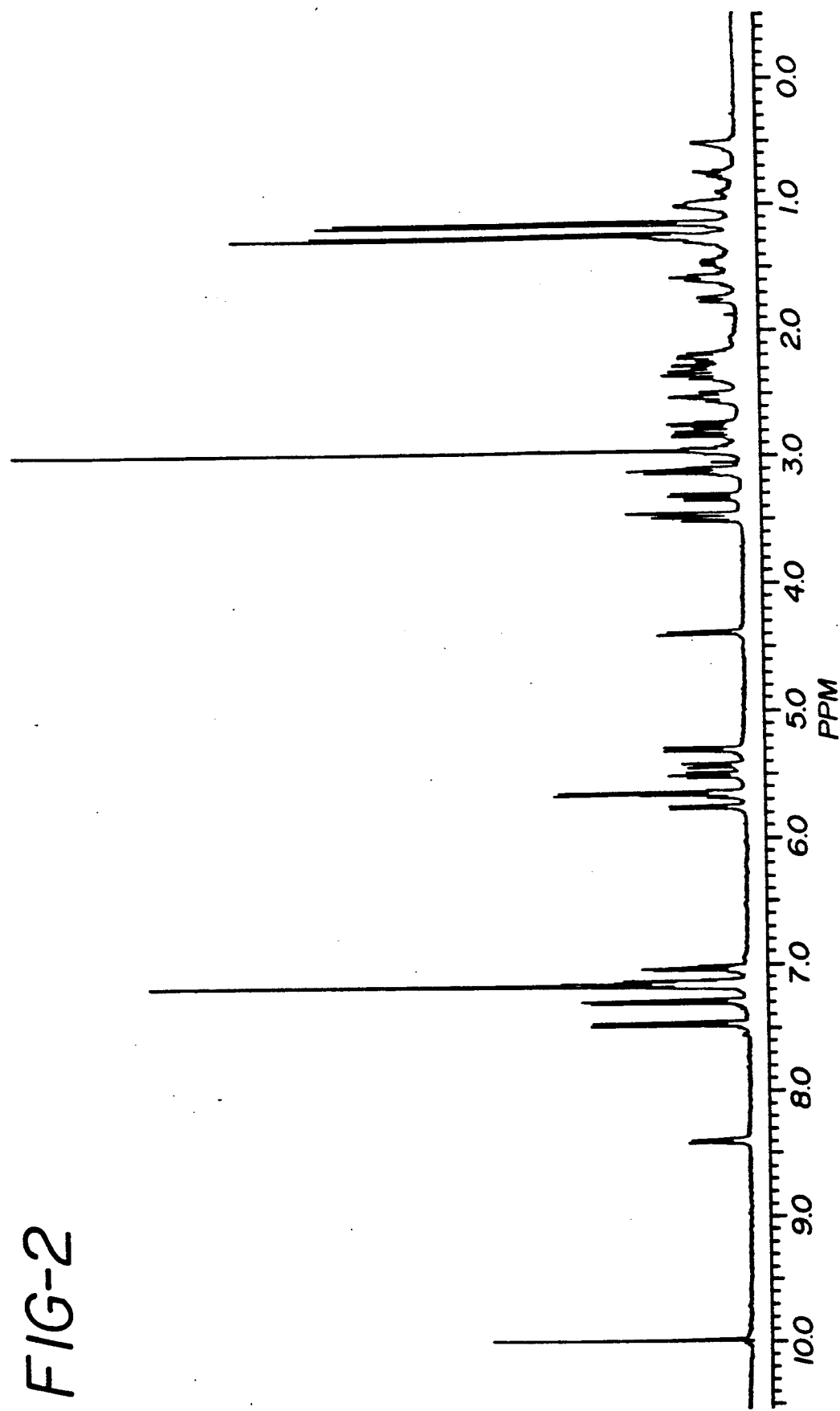
FIG. 2 is a $^1$H-NMR spectrum of minor component A.
Figure 3:
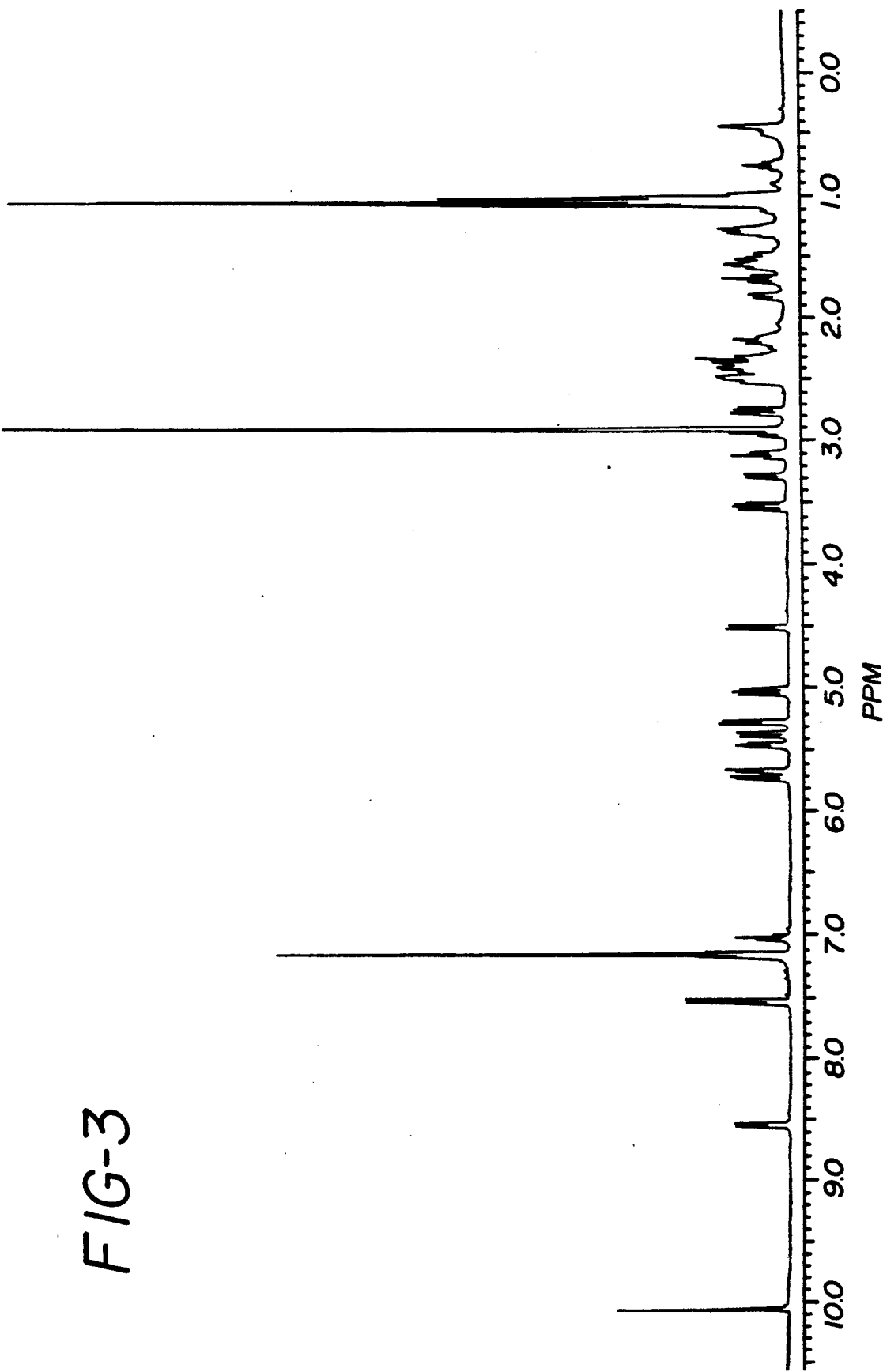
FIG. 3 is a $^1$H-NMR spectrum of minor component B.
Figure 4:
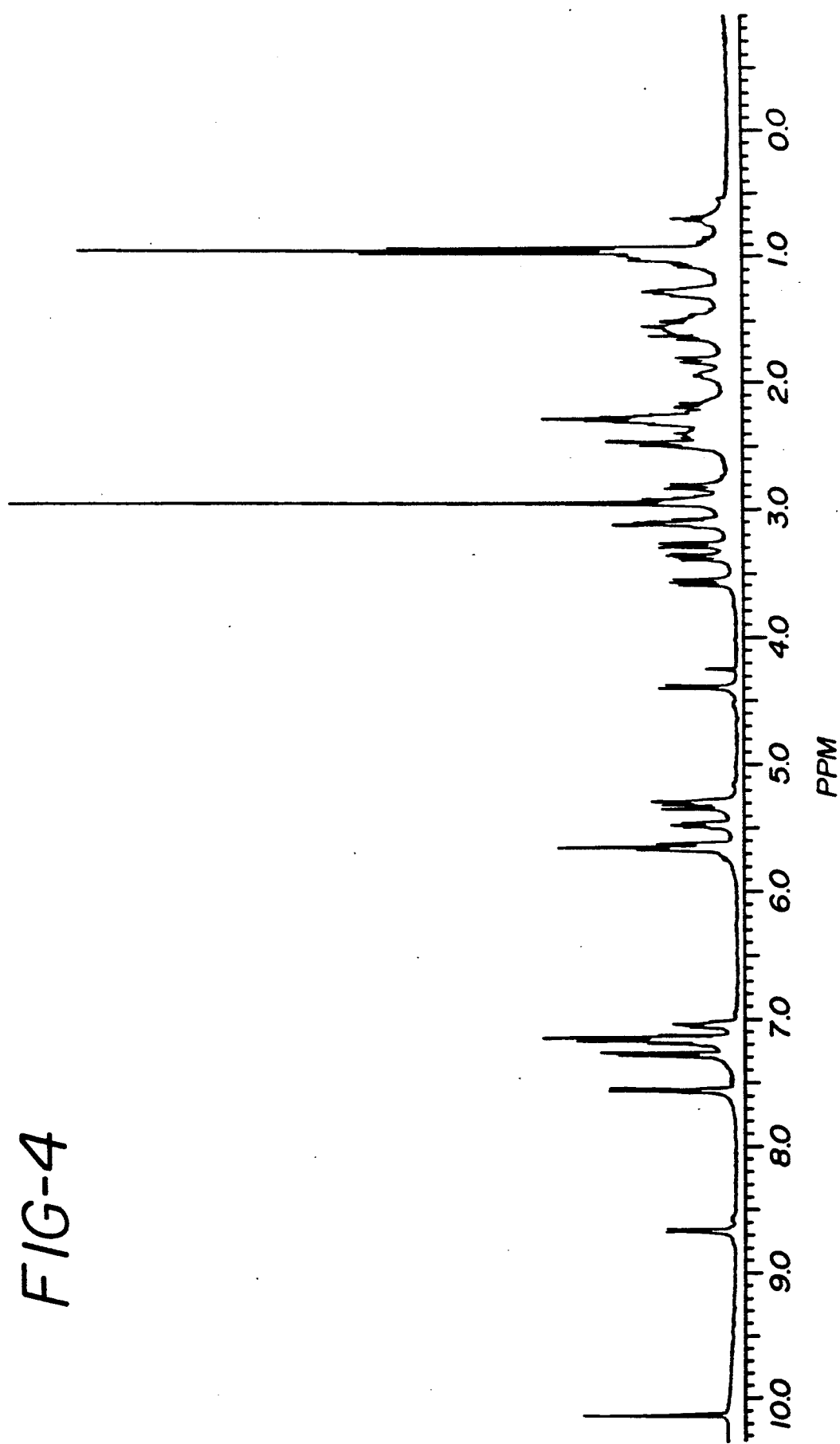
FIG. 4 is a $^1$H-NMR spectrum of minor component C.
Figure 5:
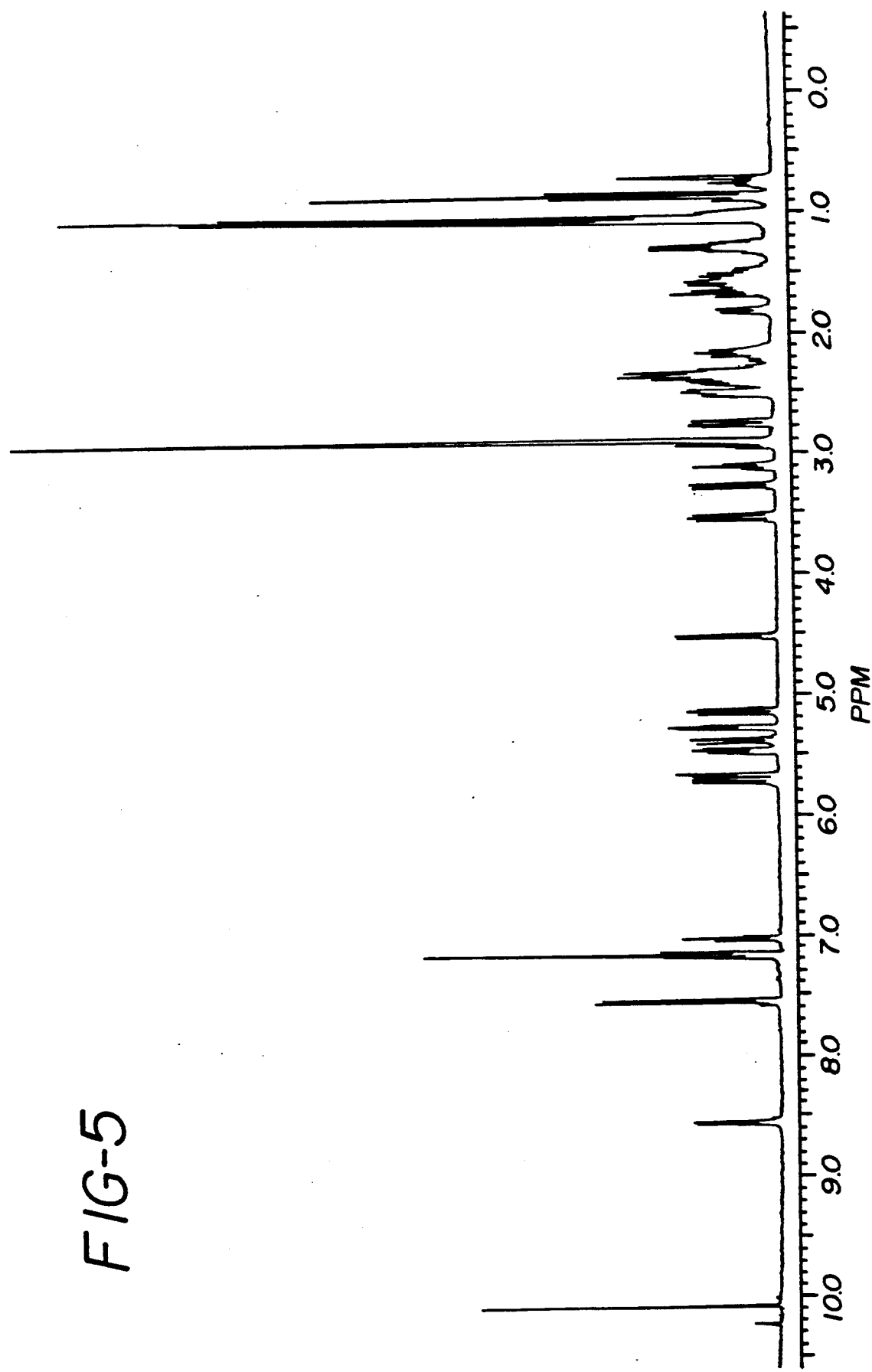
FIG. 5 is a $^1$H-NMR spectrum of minor component D.
Figure 6:
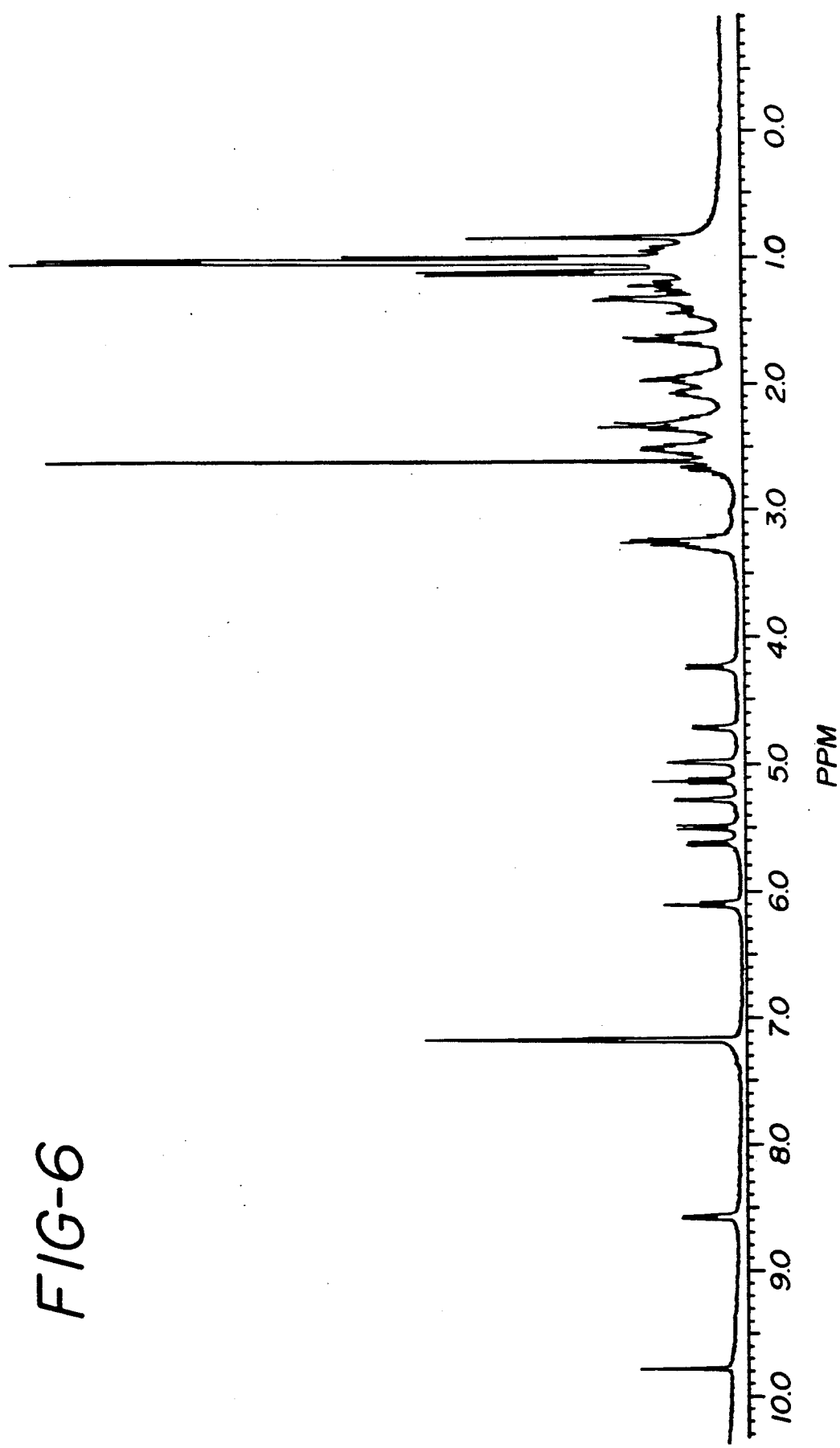
FIG. 6 is a $^1$H-NMR spectrum of minor component E.
Figure 7:
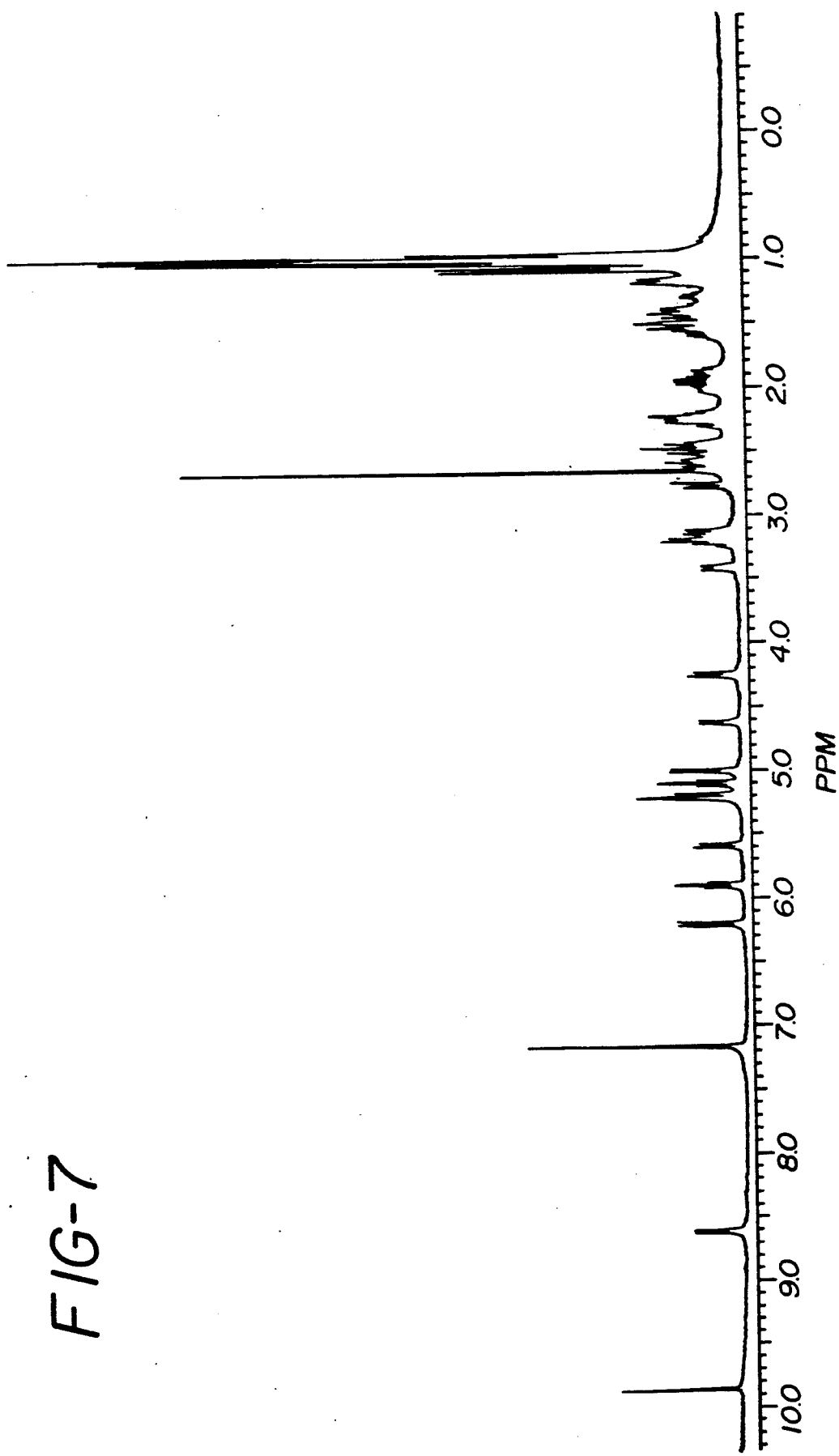
FIG. 7 is a $^1$H-NMR spectrum of minor component F.
Figure 8:
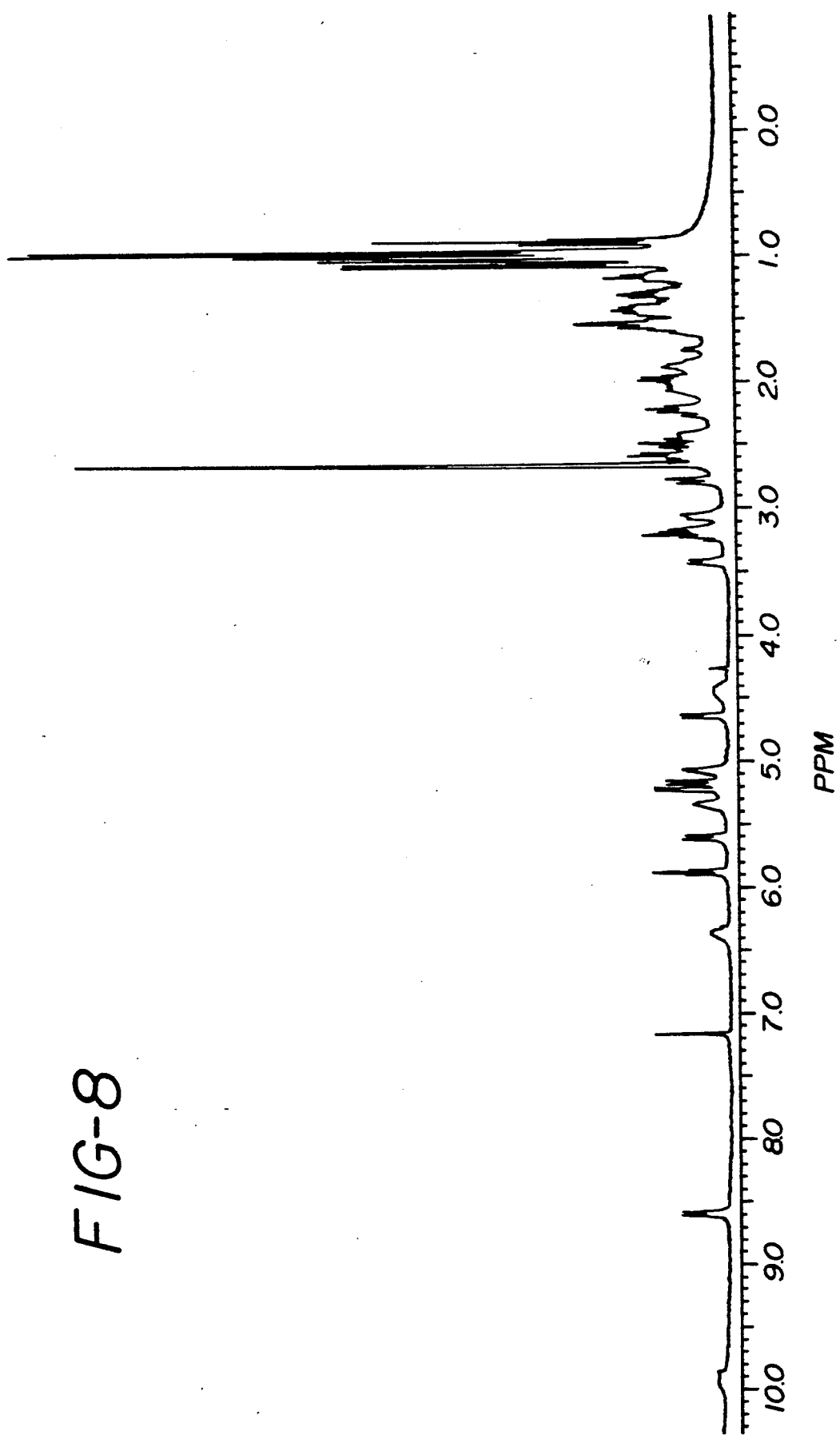
FIG. 8 is a $^1$H-NMR spectrum of minor component G.

It has now been found that the compound having Formula I and several minor related compounds are produced by the controlled aerobic fermentation of *Streptomyces silvensis* ATCC No. 53525 or ATCC No. 53526.

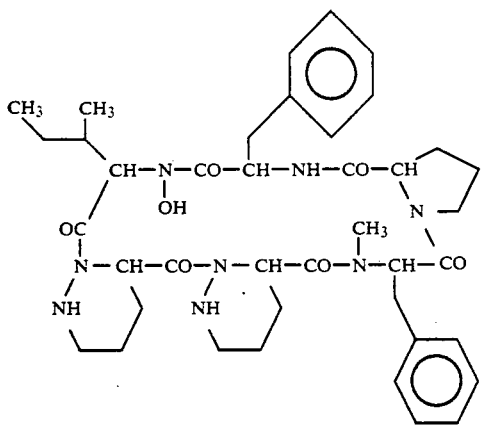

(I)

The compound of Formula I, its synthetic analogues and the minor related compounds are antagonists of oxytocin and vasopressin. Oxytocin antagonists are useful in the treatment of preterm labor. Vasopressin antagonists are useful in the treatment and prevention of disorders of the renal and cardiovascular system of animals, including humans. The preparation and isolation of the compound of Formula I is described. Also described is the in vitro activity of the compound of Formula I, its analogues and the minor related components as antagonists of oxytocin and vasopressin.

DETAILED DESCRIPTION

The compound of Formula I and several minor related compounds are produced by the controlled aerobic fermentation of a novel strain of *Streptomyces silvensis*, ATCC No. 53525 or ATCC No. 53526.

The microorganism ATCC No. 53525 or ATCC No. 53526 was isolated from a forest floor soil in Pimpri, India. A deposit under the Budapest Treaty of a biologically pure culture of this microorganism was made with the American Type Culture Collection, Rockville, Md., on July 29, 1986 under Accession No. ATCC 53525. The microorqanism ATCC No. 53526 is a naturally occurring subisolate of ATCC No. 53525.

The culture characteristics of this organism were compared with culture descriptions of Streptomyces species described in Bergey's *Manual of Determinative Bacteriology*, Eighth Edition, 1974, Williams & Wilkens, Baltimore, MD and the International Streptomyces Project reports, Shirling, E. B. & D. Gottlieb: Cooperative description of type cultures of Streptomyces. II. Species description from first study. Intern. J. Syst Bacteriol. 18: 69 189, 1968;

Shirling, E. B. & D. Gottlieb: Cooperative description of type cultures of Streptomyces. III. Additional species descriptions from first and second studies. Intern. J. Syst. Bacteriol. 18: 279 392, 1968;

Shirling, E. B. & D. Gottlieb: Cooperative description of type cultures of Streptomyces. IV. Species descriptions from the second, third, and fourth studies. Inter. J. Syst. Bacteriol. 19: 391 512, 1969; V. Additional.

Descriptions, Inter J. Syst. Bacteriol. 22: 265 394, 1972.

The organism has characteristics in common with *Streptomyces fradiae* but there are significant differences, such as color of vegetative mycelia and development of green color on specific media and at certain temperatures.

As a result of the comparisons, it was concluded that the organism is a novel species of Streptomyces and has, therefore, been designed *Streptomyces silvensis* sp. nov.

The cultural characteristics of *Streptomyces silvensis*, ATCC No. 53525 or ATCC No. 53526, are as shown in Table I, below:

TABLE I

Cultural Characteristics of ATCC No. 53526

(V = vegetative growth; A = aerial mycelium;
SP = soluble pigment)
Morphology: Sporophores from tufts of spore chains showing hooks, loops and loose, open coils. Spore surface is smooth (TEM).

Yeast extract-malt extract agar (ISP Medium 2)
V: Reverse - Yellowish tan edged with light orange and pink
A: Mixture of cream, coral and pink
SP: None

Oatmeal agar (ISP Medium 3)
V: Reverse - reddish orange
A: Light pink and cream becoming deep rose as culture ages
SP: None

Inorganic salts starch agar (ISP Medium 4)
V: Reverse - Coral mixed with pink
A: Pale pink mixed with cream, becoming deeper rose as culture ages
SP: None

Glycerol asparagine agar (ISP Medium 5)
V: Reverse - Coral mixed with orange and pink
A: Coral mixed with orange, pink and cream
SP: None

Peptone-iron-yeast extract agar (ISP Medium 6)
V: Tan
A: None
SP: None
Melanin: None

Tyrosine agar (ISP Medium 7)
V: Reverse - greenish tan
A: Pale greenish white edged with white and pink tones
SP: None

Egg albumin agar
V: Reverse - bright greenish yellow
A: Yellow with a green tinge
SP: None

Czapek Dox agar
V: Reverse - Cream to light orange
A: Cream with yellow tones
SP: None

Carbon utilization
Pridham-Gottlieb basal medium + 1% carbon source:
+ = growth; ± = growth poor or questionable;
− = no growth as compared to negative control
(no carbon source)

| | |
|---|---|
| Glucose | + |
| Arabinose | ± |
| Cellulose | − |
| Fructose | + |
| Inositol | + |
| Lactose | − |
| Maltose | + |
| Mannitol | + |
| Mannose | + |
| Raffinose | − |
| Rhamnose | − |
| Sucrose | + |
| Xylose | + |

Temperature range (Yeast extract-dextrose + salts agar)
28° C. - Good vegetative and aerial growth with sporulation
37° C. - Good vegetative and aerial growth with sporulation
42° C. - No growth
50° C. - No growth Oxygen requirements (Stab culture in yeast extract-dextrose + salts agar)

TABLE I-continued
Cultural Characteristics of ATCC No. 53526

Aerobic

All reading taken after three weeks at 28° C. unless notes otherwise. pH of all media approximately neutral (6.8-7.2).

Color number designations taken from Color Harmony Manual, 1958, 4th Edition, Container Corporation of America, Chicago, Ill.

Cultural Characteristics of ATCC No. 53525

(V = vegetative growth; A = aerial mycelium; SP = soluble pigment)
Morphology: Sporophores from tufts of spore chains showing hooks, loops and loose, open coils. Spore surface is smooth.

Yeast estract-malt extract agar (ISP Medium 2)
- V: Reverse - deep reddish orange edged with red. Substrate mycelium becomes yellow with addition of NaOH and reverts to red when acidified.
- A: A mixture of coral and cream, developing pink tones as culture ages. Center appears yellowish green when culture is incubated at 37° C.
- SP: None

Oatmeal agar (ISP Medium 3)
- V: Deep reddish orange
- A: Pink and coral becoming deep rose as culture ages
- SP: None

Inorganic salts-starch agar (ISP Medium 4)
- V: Reverse - Bright reddish orange edged with red
- A: Pale coral becoming deep rose as culture ages
- SP: None

Glycerol asparagine agar (ISP Medium 5)
- V: Reverse - Orange
- A: Pale coral and orange edged with deeper orange
- SP: None

Peptone iron-yeast extract agar (ISP Medium 6)
- V: Tan
- A: Sparse, whitish
- SP: None
- Melanin: None

Tyrosine agar (ISP Medium 7)
- V: Reverse - orange mixed with olive green
- A: Center is yellowish green edged with orange and coral
- SP: None

Egg albumin agar
- V: Reverse - colorless mixed with green and edged with pink
- A: Lime green edged with mixture of pink and cream
- SP: None

Czapek Dox agar
- V: Reverse - pink mixed with light orange and coral
- A: Pale pink mixed with light orange and coral
- SP: None

Carbon utilization
Pridham-Gottlieb basal medium + 1% carbon source:
+ = growth; ± = growth poor or questionable;
− = no growth as compared to negative control (no carbon source)

| | |
|---|---|
| Glucose | + |
| Arabinose | + |
| Cellulose | − |
| Fructose | + |
| Inositol | + |
| Lactose | ± |
| Maltose | + |
| Mannitol | + |

-continued
Cultural Characteristics of ATCC No. 53525

| | |
|---|---|
| Mannose | + |
| Raffinose | ± |
| Rhamnose | ± |
| Sucrose | + |
| Xylose | + |

Temperature range (Yeast extract-dextrose + salts agar)
28° C. - Good vegetative and aerial growth with sporulation
37° C. - Good vegetative and aerial growth with sporulation
42° C. - No growth
50° C. - No growth

Oxygen requirements (Stab culture in yeast extract-dextrose + salts agar)

Aerobic

All readings taken after three weeks at 28° C. unless noted otherwise. pH of all media approximately neutral (6.8-7.2).

Color number designations taken from Color Harmony Manual, 1958, 4th Edition, Container Corporation of America, Chicago, Ill.

Fermentation Conditions

The compound of Formula I and the minor related compounds are produced by the aerobic fermentation of suitable aqueous nutrient media under controlled conditions via inoculation with a culture of the organism *Streptomyces silvensis*, ATCC No. 53525 or ATCC No. 53526. The media contains sources of assimilable carbon, nitrogen, and inorganic salts. In general, carbohydrates (for example, glucose, fructose, maltose, sucrose, xylose, and the like) can be used either alone or in combination as sources of assimilable carbon in the nutrient medium. These carbon sources may be used individually or combined in the medium.

Generally, many proteinaceous materials may be used as nitrogen sources for the fermentation process. Suitable nitrogen sources include, for example, yeast hydrolysates, primary yeast, soybean meal, cottonseed flower, hydrolysates of casein, cornsteep liquor, distillers solubles or tomato paste, and the like.

Among the nutrient in organic salts which can be incorporated in the culture medium are customary salts capable of yielding sodium, potassium, ammonium, calcium, phosphate, sulfate, chloride, carbonate, and the like ions. Also included are trace metals such as cobalt, manganese, iron, magnesium, and the like.

It should be noted that the nutrient medium described herein are merely illustrative of the wide variety of medium which may be employed, and are not intended to be limiting.

The fermentation is carried out at temperatures ranging from about 20° C. to 37° C.; however, for optimum results it is preferable to conduct the fermentation at temperatures of about 28° C. The pH of the nutrient medium for growing the *Streptomyces silvensis*, ATCC No. 53525 or ATCC No. 53526, cultures and producing the vasopressin antagonist of Formula I and several minor related compounds can vary from about 6.8 to 7.4.

It is to be understood that for the fermentation production of the compound of Formula I and several minor related compounds, the present invention is not limited to the use of *Streptomyces silvensis*, ATCC No. 53525 or ATCC No. 53526. It is especially desired and intended that there be included within the scope of this invention the use of other natural or artificial mutants produced or derived from the described cultures, or other variants or species of the genus Streptomyces insofar as they can produce the compound of Formula I or any of its several minor related compounds. The artificial production of mutant species or strains of Streptomyces from ATCC No. 53525 or ATCC No. 53526 may be achieved by conventional, physical or chemical mutagens, for example, ultraviolet irradiation of the described cultures, or nitrosoguanidine treatment and the like. Recent recombinant DNA techniques such as protoplast fusion, plasmid incorporation, chromosome fragment incorporation and the like may also prove useful.

In a preferred embodiment of the present invention, the compound of Formula I and its several minor related compounds are produced by the controlled aerobic fermentation of the microorganism *Streptomyces silvensis*, ATCC No. 53525 or ATCC No. 53526. Fermentation should be conducted at a temperature range of from about 20° C. to 37° C., preferably at about 28° C. Generally, the composition of the assimilable nutrient medium may be varied over a wide range. The essential nutrient ingredients are a carbon source and a nitrogen source. Other essential nutrients are provided via mineral salts such as the chlorides, nitrates, sulfates, carbonates and phosphates of sodium, potassium, ammonium and calcium. The nutrient medium may also contain sources of inorganic trace elements such as magnesium, iron, copper, manganese, zinc, cobalt, and the like.

Typical sources of carbon include: glucose, oils, organic acids, dextrin, starches, glycerol and the like. Typical nitrogen sources include: amino acids, vegetable meals, and extracts (e.g , malts, soy, cotton seed, figs, tomato, corn, etc.), animal viscera, various hydrolysates (e.q., casein, yeast, etc.) and industrial by-products such as lard water and distillers solubles.

The maximum yield of the compound of Formula I can be achieved within about 24 to 200 hours, usually in about 72 to 96 hours, of fermentation under optimum conditions. The inoculum for the fermentation may be provided from vegetative growth in a medium which supports rapid growth of the microorganism, or directly from spores.

Following fermentation, the accumulated compound of Formula I may be separated from its several minor related compounds and recovered from the broth by conventional chromatographic means.

The fermentation broth is filtered to separate mycelia from liquid supernatant. These are extracted as follows:

A. The supernatant is shaken with an equal volume of a moderately polar solvent, immiscible in water such as: chloroform, ethyl acetate, methyl ethyl ketone, and the like. The layers are allowed to settle; the organic phase contains all of the compound of Formula I initially located within the supernatant.

B. The mycelia are stirred vigorously (homogenized) with several volumes of acetone, ethyl acetate, methyl ethyl ketone or the like. These solvents will dissolve most of the compound of Formula I located within the mycelia.

The combined mycelial and supernatant organic extracts are then concentrated to a small volume under reduced pressure. The resultant mass is subjected to a series of solvent partitioning and washing steps. Solvents of choice include petroleum ether, hexane, ether, methylene chloride, methanol and similar solvents. Adsorption and partition chromatographies, gel filtration, reversed phase liquid chromatography and the like may be used, in conjunction with eluents of proper polarity and solubilizing characteristics to afford the compound of Formula I as an off-white powder.

The several minor components of the fermentation broth may be recovered by a similar application of a series of chromatographic techniques. Seven minor components, herein referred to as A to G have thus far been isolated from the fermentation broth of *Streptomyces silvensis*, ATCC No. 53525 or ATCC No. 53526. By weight, these minor components, combined, amount to about five weight percent of the isolated compound of Formula I.

A number of different nutrient media may be employed in the fermentation of *Streptomyces silvensis*, ATCC No. 53525 or ATCC No. 53526. Variation of the medium or the microorganism will vary the yield of the compound of Formula I and/or its rate of production. Variation of the medium or the microorganism may also increase or decrease the type and amount of several minor related compounds present in the broth. The preferred media compositions are set forth in Table II.

TABLE II

| MEDIA | |
|---|---|
| KE | |
| Glucose | 1.0 g/L |
| Dextrin | 10.0 g/L |
| Beef Extract | 3.0 g/L |
| Ardamine | 5.0 g/L |
| Nzamine | 5.0 g/L |
| MgSO$_4$.7H$_2$O | 0.05 g/L |
| Phosphate Buffer | 2.0 ml |
| CaCO$_3$ | 0.5 g/L |
| pH 7.0-7.2 | |
| Phosphate Buffer | |
| KH$_2$PO$_4$ | 91.0 g/L |
| Na$_2$HPO$_4$ | 95.0 g/L |
| pH 7.0 | |
| YME | |
| Yeast Extract (Difco) | 4.0 g/L |
| Malt Extract (Difco) | 10.0 g/L |
| Glucose | 4.0 g/L |
| Agar | 20.0 g/L |
| pH 7.0-7.4 | |
| KI | |
| Glucose | 10.0 g/L |
| L-Asparagine | 1.0 g/L |
| Yeast Extract | 1.0 g/L |
| 25 mM MOPS | |
| p-2000 - 1 drop/50 ml | |
| pH 7.2-7.4 | |
| NPA-4 | |
| Asparagine | 1.0 g/L |
| Edamine | 2.5 g/L |
| Primatone | 2.5 g/L |
| Yeast Extract | 5.0 g/L |
| Malt Extract | 10.0 g/L |
| Sucrose | 5.0 g/L |
| CaCO$_3$ | 5.0 g/L |
| pH 7.2-7.4 | |
| NPA-6 | |
| Asparagine | 1.0 g/L |
| Primatone | 2.5 g/L |
| Yeast Extract | 5.0 g/L |
| Glucose | 10.0 g/L |
| CaCO$_3$ | 5.0 g/L |
| Mineral Salts | 250.0 ml |
| pH 7.2-7.4 | |
| Mineral Salts | |
| KCl | 0.74 g/L |
| CaCl$_2$ | 0.02 g/L |
| NaH$_2$PO$_4$ | 1.4 g/L |
| Citric Acid | 0.38 g/L |

TABLE II-continued

| MEDIA | |
|---|---|
| MgCl$_2$ | 0.25 g/L |
| Na$_2$SO$_4$ | 0.36 g/L |
| trace elements | 50 ml |
| Trace Elements | |
| Con. HCl | 10 ml/L |
| FeCl$_3$.6H$_2$O | 5.4 g/L |
| MnCl$_2$.2H$_2$O | 2.0 g/L |
| CuCl$_2$.2H$_2$O | 0.17 g/L |
| CoCl$_2$.6H$_2$O | 0.48 g/L |
| H$_3$BO$_4$ | 0.06 g/L |
| Na$_2$MoO$_4$ | 0.2 g/L |

The terms "seed" and "production" media are employed as terms of art. Generally, a seed medium supports rapid growth of the microorganism and an aliquot (seed) of this medium is used to inoculate a production medium for a large scale fermentation.

The following examples describe the fermentation production and isolation of the compound of Formula I and its several minor related compounds. These examples are merely illustrative, they are not intended to limit the scope of the invention.

EXAMPLE 1

A frozen vial (−80° C.) of the culture ATCC No. 53525 was thawed and the entire contents (2.0 ml) was inoculated into 54 ml of KE seed medium in a baffled 250 ml Erlenmeyer flask. This seed was incubated at 28° C., 220 rpm for 4 days. A 4% inoculum was then used to inoculate each of 4 2L baffled Erlenmeyer flasks containing 250 ml of NPA 6 medium. These flasks were incubated at 28° C., 220 rpm for 4 days. Upon harvest, the 4 flasks were pooled.

EXAMPLE 2

A frozen vial (−80° C.) of the culture ATCC No. 53525 was thawed and the entire contents (2.0 ml) was inoculated into 54 ml of KE seed medium in a baffled 250 ml Erlenmeyer flask. This seed was incubated at 28° C., 220 rpm for 1 day. A 4% inoculum was used to inoculate another KE seed flask, which was incubated at 28° C., 220 rpm for 3 days. A 4% inoculum of this seed was then used to inoculate each of 4 2L baffled Erlenmeyer flasks containing 250 ml of NPA-4 medium. After incubation at 28° C., 220 rpm for 4 days, these flasks were harvested and pooled.

EXAMPLE 3

A frozen vial (−80° C.) of the culture ATCC No. 53525 was thawed and the entire contents (2.0 ml) was inoculated into 54 ml of KE seed medium in a baffled 250 ml Erlenmeyer flask. This seed was incubated at 28° C., 220 rpm for 2 days. A 4% inoculum was used to inoculate another KE seed flask, which was incubated at 28° C., 220 rpm for 2 days. A 4% inoculum of this seed was used to inoculate 4 2L baffled Erlenmeyer flasks containing 250 ml of NPA-4 medium. After incubation at 28° C, 220 rpm for 4 days these flasks were harvested and pooled.

EXAMPLE 4

The fermentation batch from Example 1 was agitated with methylethylketone (1.2 volumes) for one-half hour. After allowing the layers to settle and separate, the organic phase was evaporated to dryness. The residue was redissolved in a small amount of methanol and fractionated by gel filtration on a 70 cc column packed with Sephadex LH 20. Elution with methanol afforded semi-purified compound of Formula I at an elution volume of 0.51–0.63 column volumes.

The fractions containing the compound of Formula I were dried down, redissolved in 0.5 ml of methanol and further fractionated by RP-HPLC (reverse-phase high performance liquid chromatography) on a Whatman Magnum 9 ODS 3 column eluted at 8 ml/min. and 40° C. with a 30 minute gradient of acetonitrile (from 35% to 100%).

Purified compound of Formula I was obtained after 8.5 column volumes of eluate. The appropriate fractions were dried down under vacuum and examined spectroscopically.

EXAMPLE 5

Fermentation broth from Example 2 was filtered through a Celite filtering aid. Cells and broth filtrate were extracted separately with vigorous shaking with successive portions of ethyl acetate. The two extracts were combined, evaporated to dryness, reconstituted in a small volume of methylene chloride-methanol (3:1) and fractionated at high speed through a 100 cc bed of E. Merck silica gel 60 packed in methylene chloride methanol (95:5). Elution with a step gradient of methanol in methylene chloride from 5% to 100% afforded semi purified minor Components A and B in the 10% methanol eluate. This solution was evaporated, the residue redissolved in 0.5 ml of methanol and final purification was achieved by HPLC (Whatman Magnum 9 ODS-3 column, eluted at 8 ml/min and 40° C for 15 minutes with 35% aqueous acetonitrile, followed by a linear gradient of acetonitrile to 100% over the next 30 minutes). Pure Component A (6 mg) was obtained at 14 column volumes of eluate and Component B (35 mg) at 14.5 column volumes.

The presence of further members of this cyclic hexapeptide family was recognized during the work-up of this fermentation, however, their low concentration precluded isolation. Isolation was achieved in later batches.

EXAMPLE 6

Fermentation batches from Example 2 and from Example 3 were filtered through filter-aid. The cells, containing over 85% of the components of interest, were extracted in a homogenizer twice with ethyl acetate. The combined extracts were evaporated down under vacuum. The solid residue was redissolved in 10 cc of methylene chloride-methanol (92:8) and slowly passed through a 100 cc column packed with E. Merck silica el 60 equilibrated with 8% methanol in methylene chloride. Elution of the column was carried out with the same solvent mixture. Components E, F and G were obtained together in Fraction I; Fraction II contained the crude Component D.

Fraction I was evaporated to dryness, reconstituted in 0.5 ml of methanol, and this solution was fractionated at 42° C on a Whatman ODS-3 Magnum-9 column eluted at 8 ml/min. for 15 minutes with acetonitrile water 4:6) followed by a 20 minute linear gradient up to a 50:50 mixture. Pure Component F was obtained after 10 column volumes of eluent; pure Component G (12 mg) after 13 column volumes; and pure Component E (8 mg) after 17 column volumes. Each fraction was concentrated down under vacuum and freeze-dried in preparation for spectroscopic analyses.

Fraction II from above was evaporated, redissolved in 0.5 ml of methanol and partial purification was obtained by passing this solution through a Magnum-9 ODS 3 column using 60% aqueous acetonitrile at 42° C delivered at 8 ml/min. Final purification of Component D was accomplished by HPLC on the same column, elating with acetonitrile-water 1:1 at 8 ml/min and 42° C. Compound was obtained as a broad peak eluting at approximately 16-17 column volumes.

EXAMPLE 7

Though its presence had been detected by HPLC in earlier fermentations, the isolation of Component C was accomplished only during the purification of gram quantities of the compound of Formula I from large scale batches.

Approximately 110 liters of fermentation broth [14 L batches +70 L batch]were centrifuged through a Sharples continuous feed centrifuge. The compacted cells, which contained some 95% of the compounds of interest, were extracted as follows: twice in succession with 5 liters of ethyl acetate, twice with 50% methanol in ethyl acetate, once with methanol and finally three times in succession with ethyl acetate-water (1:1). The last three extracts were combined and the layers allowed to settle. The ethyl acetate phase was collected and concentrated down to a thick oil. This was triturated with 500 cc methylene chloride methanol and left to stand at −20° C. The resulting heavy suspension was filtered to remove the fluffy solids that had formed (containing only impurities) and the filtrate was evaporated down. The gummy residue was redissolved in 80 cc of methanol and passed through a 4.2 liter Sephadex LH 20 column (in methanol). Bulk compound of Formula I mixed with the Component C was eluted between 0.66 and 0.77 column volumes. The unconcentrated fractions were kept at 4° C. overnight. More impurities were removed by filtration.

The soluble portion was dried to a solid under vacuum. The residue, taken up in 10 cc of methylene chloride methanol 19:1, was fractionated on 450 cc E. Merck silica gel 60 previously equilibrated with 3% methanol in methylene chloride. Elution of the column was carried out at 10 ml/min with the same solvent mixture. The compound of Formula I and Component C were obtained together in a broad fraction (volume of elution: 1-1.5 column volumes). The appropriate fractions were dried down.

Separation of the two components was achieved by HPLC: a series of 0.5 ml aliquots of methanolic solution of the solids obtained after the silica gel step were fractionated on a ODS-3 column (50 cm×9 mm) eluted at 40° C. with 50% aqueous acetonitrile delivered at 8 ml/min. Component C was obtained as a very broad peak centering around retention time 40 minutes (volume of retention 16 column volumes). These fractions were extracted with ethyl acetate, concentrated on a rotary evaporator and the resulting suspension was freeze-dried to yield the purified Component C.

EXAMPLE 8

Characterization of the Compound of Formula I and Minor Components

The solid material obtained in Example 4 above was characterized by high resolution mass spectrometry and nuclear magnetic resonance spectroscopy, as discussed below. From these data, the structure of Formula I was assigned:

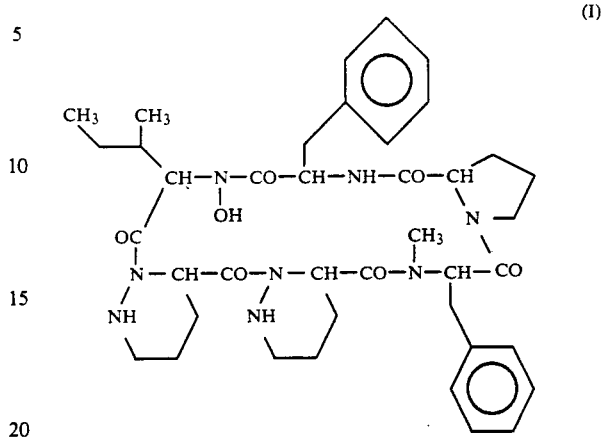

The structure I as shown above is intended to encompass all possible stereoisomers. The structures of the analogues and minor components also are intended to encompass all possible stereoisomers.

1. Mass Spectral Data

All mass spectra were recorded on a Finnigan-MAT212 instrument by electron impact at 90 eV. Acid hydrolyses were carried out in 6N hydrochloric acid in tightly capped vials at 100° C. for 18 hours. The amino acids were identified by GC-MS as the trimethylsilyl derivatives. Trimethylsilyl derivatives were prepared with a 1:1 mixture of BSTFA pyridine at room temperature. Exact mass measurements were made on the same instrument at high resolution by the peak matching method using perfluorokerosene (PFK) as internal standard.

2. $^1$H-NMR Spectra

The spectra were recorded at ambient temperature in $C_6D_6$ on a Varian XL 400 spectrometer. Chemical shifts are shown in ppm relative to tetramethylsilane (TMS) at zero ppm using the solvent peak at 7.15 ppm as internal reference. The spectrum for the compound of Formula I is shown in FIG. 1.

3. $^{13}$C-NMR Spectra

Spectra were recorded in $CD_2Cl_2$ or $C_6D_6$ at ambient room temperature on a Varian XL-400 NMR spectrometer. Chemical shifts are given in ppm relative to tetramethylsilane at zero ppm using the solvent peak as internal reference at 53.8 ppm for $CD_2Cl_2$ and 128.0 ppm for $C_6D_6$.

Formula I compound: $CD_2Cl_2$) 12.1, 15.7, 20.5, 21.3, 24.4, 24.9, 25.5, 26.4, 26.7, 31.7, 34.2, 35.1, 37.8, 46.65, 46.74, 47.3, 47.5, 48.6, 50.4, 56.1, 60.2, 60.9, 126.8, 127.0, 128.54 (2x), 128.6 (2x), 129.6 (2x), 129.7 (2x), 137.56, 137.63, 171.0 (2x), 171.3, 171.8, 173.5, and 174.7 ppm.

Component C: $C_6D_6$) 20.7, 20.9 (2x), 23.7, 24.2, 24.4, 24.7, 24.8, 26.2, 32.1, 35.4, 36.2, 36.9, 45.4, 46.1, 46.6, 47.0, 49.5, 50.5, 58.1, 58.5, 59.6, 126.7, 126.8, 127.5–129.5 (obsc), 129.7 (2x), 130.4 (2x), 137.5, 138.7, 169.0, 170.2, 171.7 (2x), 173.3, and 174.2 ppm.

Component D: ($C_6D_6$) 10.8, 15.4, 20.7, 21.0, 21.07, 23.8, 24.2, 24.4, 24.8, 25.0, 26.5 (2x), 32.1, 35.1, 35.5, 36.3, 45.4, 46.2, 46.7, 47.0, 49.5, 54.4, 58.1, 58.7, 59.7, 126.7, 128.6 (2x), 130.4 (2x), 138.8, 169.0, 170.2, 172.2, 172.6, 173.3, and 174.3 ppm.

Component G: $C_6D_6$) 11.0, 15.1, 20.4, 20.7, 22.9, 23.1, 23.7, 24.4, 25.1 (2x), 25.3, 26.2, 26.4, 29.9, 31.0, 36.2, 36.4, 38.4, 44.1, 46.8, 48.2, 51.4, 52.7, 53.4, 54.3, 57.4, 58.7, 60.1, 170.5, 171.7, 172.0, 172.3, 173.9, and 174.1 ppm.

Definitions

The following abbreviations will be used for the amino acid residues:

| | |
|---|---|
| ILE | isoleucine |
| NOH—PHE | N-hydroxy-phenylalanine |
| NOH—ILE | N-hydroxy-isoleucine |
| NOH—LEU | N-hydroxy-leucine |
| NOH—VAL | N-hydroxy-valine |
| N—MeLEU | N-methyl-leucine |
| N—MePHE | N-methyl-phenylalanine |
| PHE | phenylalanine |
| PIP | HN—CH—CO$_2$H / \ HN CH$_2$ \ / CH$_2$CH$_2$ |
| PRO | proline |
| VAL | valine |

The structure of the component of formula I was investigated in detail and the structures of the other components were assigned by comparison of critical data.

| | Formula I Compound | | |
|---|---|---|---|
| HR-MS | FOUND | CALCULATED | FORMULA |
| | 758.4135 | 758.4115 | $C_{40}H_{54}N_8O_7$ |
| | 740.4007 | 740.4010 | $C_{40}H_{52}N_8O_6$ |
| | 628.3380 | 628.3373 | $C_{35}H_{44}N_6O_5$ |
| | 544.2681 | 544.2686 | $C_{31}H_{36}N_4O_5$ |
| | 517.2792 | 517.2815 | $C_{30}H_{37}N_4O_4$ |
| | 487.2467 | 487.2471 | $C_{29}H_{33}N_3O_4$ |
| | 376.1759 | 376.1787 | $C_{23}H_{24}N_2O_3$ |
| | 257.1287 | 257.1290 | $C_{15}H_{17}N_2O_2$ |
| | 229.1312 | 229.1341 | $C_{14}H_{17}N_2O$ |
| | 229.1103 | 229.1103 | $C_{14}H_{15}NO_2$ |
| | 134.0970 | 134.0970 | $C_9H_{12}N$ |

The compound of Formula I contains one equivalent each of PHE, N-MePHE, and PRO by hydrolysis. NMR indicates in addition two equivalents of PIP and one NOH-ILE. These six amino acids joined by peptide bonds in a cyclic structure account for the empirical formula. The complete peptide sequence is as follows:

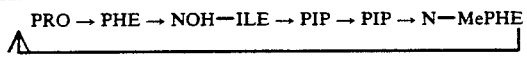

PRO → PHE → NOH—ILE → PIP → PIP → N—MePHE

Data for Components A, B, C, and D
(Data for Formula I Compound Included for Comparison)
HR—MS

| Compound | Found | Calculated | Molecular Formula |
|---|---|---|---|
| Formula I | — | — | $C_{40}H_{54}N_8O_7$ |
| A | 744.3971 | 744.3959 | $C_{39}H_{52}N_8O_7$ |
| B | 710.4117 | 710.4115 | $C_{36}H_{54}N_8O_7$ |
| C | 758.4113 | 758.4115 | $C_{40}H_{54}N_8O_7$ |
| D | 724.4267 | 724.4272 | $C_{37}H_{56}N_8O_7$ |

| | Amino Acid Composition | | |
|---|---|---|---|
| Compound | AA-1 | AA-2 | AA-3 |
| Formula I | PIP | PIP | N—MePHE |
| A | PIP | PIP | N—MePHE |
| B | PIP | PIP | N—MePHE |
| C | PIP | PIP | N—MePHE |
| D | PIP | PIP | N—MePHE |

| Compound | AA-4 | AA-5 | AA-6 |
|---|---|---|---|
| Formula I | PRO | PHE | NOH—ILE |
| A | PRO | PHE | NOH—VAL |
| B | PRO | VAL | NOH—LEU |
| C | PRO | PHE | NOH—LEU |
| D | PRO | ILE | NOH—LEU |

| | | Critical Fragment Ions | | | | |
|---|---|---|---|---|---|---|
| Compound | M+ | | | | | |
| Formula I | 758 | 628 | 544 | 487 | 376 | 229 |
| A | 744 | 614 | 530 | 473 | 376 | 229 |
| B | 710 | 580 | 496 | 439 | 328 | 229 |
| C | 758 | 628 | 544 | 487 | 376 | 229 |
| D | 724 | 594 | 510 | 453 | 342 | 229 |

Structures of the Minor Components A, B, C and D

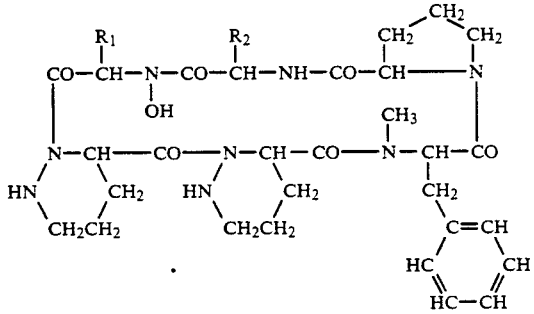

| Component | R$_1$ | R$_2$ |
|---|---|---|
| A | —CH(CH$_3$)$_2$ | —CH$_2$C$_6$H$_5$ |
| B | —CH$_2$CH(CH$_3$)$_2$ | —CH(CH$_3$)$_2$ |
| C | —CH$_2$CH(CH$_3$)$_2$ | —CH$_2$C$_6$H$_5$ |
| D | —CH$_2$CH(CH$_3$)$_2$ | —CH(CH$_3$)CH$_2$CH$_3$ |

Data for Components E, F and G
HR—MS

| Component | Found | Calc. | Molecular Formula |
|---|---|---|---|
| E | 676.4275 | 676.4272 | $C_{33}H_{56}N_8O_7$ |
| F | 692.4179 | 692.4221 | $C_{33}H_{56}N_8O_8$ |
| G | 706.4392 | 706.4378 | $C_{34}H_{58}N_8O_8$ |

Residues AA-3, AA-4, and AA-5 are seen in the acid hydrolyzate. Residues AA-1, AA-2, and AA-6 are assigned by NMR.

Amino Acid Composition

Component E: Contains one equivalent each of VAL, PRO, and N-MeLEU by hydrolysis. Two equivalents of PIP plus one equivalent of NOH-LEU (or NOH-ILE) are suggested by MS and account for the empirical formula.

Component F: Contains one equivalent each of VAL, PRO, and N MeLEU by hydrolysis. Component F contains one more oxygen than Component E. One equivalent each of PIP, a hydroxy-PIP, and NOH-LEU (or NOH-ILE) are suggested by MS and account for the empirical formula.

Component G: Contains one equivalent each of ILE, PRO, and N-MeLEU by hydrolysis. One equivalent each of PIP, a hydroxy-PIP, and NOH-LEU (or NOH ILE) are suggested by MS and account for the empirical formula. $^{13}$C-NMR suggests NOH-LEU.

The structures of Components E, F and G have not been established but are considered to be analogous to the N-MePHE containing structures.

EXAMPLE 9

Synthetic Analogue of Formula I Compound

To a magnetically stirred mixture of the compound of Formula I (2.0 grams) in methanol (46 ml) and water (19 ml) with sodium acetate (2.68 grams) under nitrogen was added TiCl₃ (20% aqueous, 1 ml). The reaction mixture turned blue. After about 35 minutes the reaction mixture was colorless and a precipitate had formed. A second 1 ml of TiCl₃ was added and after 35 minutes the solution was again colorless. Thin layer chromatography using Analtech silica plates and methylene chloride (100 ml) shaken with 10 ml aqueous concentrated ammonium hydroxide (95%) and methanol (5%) showed the presence of starting material. A third 1 ml portion of TiCl₃ was added and even though a light blue color was present after 1½ hours, a fourth 1 ml of TiCl₃ was added. Thin layer chromatography as previously described indicated that the starting material was gone. The reaction mixture was filtered through supercell, rinsed with methanol, reslurried in methanol and filtered, and the methanol was evaporated under vacuum. The material was purified by high pressure liquid chromatography and identified as the deshydroxy analogue of the Formula I compound having the following structure:

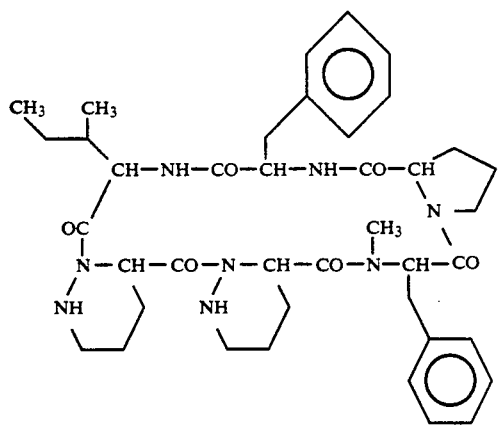

(Ia)

amino acid analysis: PRO, 0.99; Ile, 1.01; Phe, 1.00. Mass spec. 742 (M+). ¹H-NMR was consistent.

EXAMPLE 10

Oxidation Products of Synthetic Analogues

After synthesis of Example 9 compound and upon standing at room temperature oxidation products were formed having the following structures:

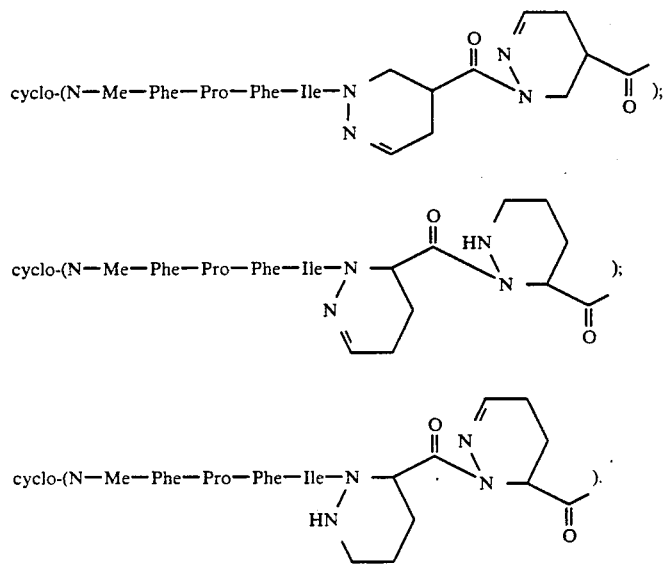

EXAMPLE 11

[³H]Oxytocin Binding Assay

Oxytocin receptors have been identified in mammalian uterine tissue through the use of in vitro radioligand binding assays. These receptor binding sites mediate the contractile response of the uterine myometrium to oxytocin. The present radioligand binding procedure has been adapted from the methods of Soloff, M. S. and Grzonka, Z., *Endocrinology* 119: 1564-1569 (1986) and Fuchs. A-R., Fuchs, F., and Soloff, M. S., *J. Clinical Endocrinology and Metabolism* 60: 37-41 (1985 and is utilized here to measure the relative affinity of test compounds for the oxytocin receptor labeled by [³H]oxytocin. The assay uses a crude membrane preparation of rat uterus as the source of oxytocin receptors. The IC₅₀ values (concentration of test compound to inhibit [³H]oxytocin binding by 50%) are determined by incubating uterine tissue with [³H]oxytocin in presence or absence of varying concentrations of compound, and as potency estimates, are inversely related to the affinities.

TABLE III

Potencies of Compounds in Oxytocin Binding Assays

| Compound | IC₅₀ (nM) [³H]OT (uterus) |
|---|---|
| Formula I | 370 ± 70 |
| Example 9 | 170 ± 15 |
| Example 10 | 42 ± 29 |

EXAMPLE 12

In Vitro Vasopressin Antagonism

The biological activity of the compound of Formula I and the minor related components is shown in TABLE IV, below. The table summarizes the in vitro potencies of the various components to compete for [3H]-vasopressin binding at two proposed vasopressin receptor subtypes ($V_1$, $V_2$), as well as to inhibit vasopressin stimulated adenylate cyclase activity, a further measure of vasopressin antagonism.

The [3H]Arginine Vasopressin Binding Assay is an in vitro procedure which was adapted from the method of Guillon et al., *Eur. J. Pharmacol.* 85: 219-304 (1982). It measures the relative affinity of the various test compounds for vasopressin receptor(s) labelled by [3H]vasopressin. Vasopressin receptors have been divided into two subtypes pharmacologically: the $V_1$(pressor) receptor found in liver and vascular smooth muscle and the $V_2$(antidiuretic)receptor found in kidney medulla. The binding assay uses a crude membrane preparation of rat liver ($V_1$ receptor) or kidney medulla ($V_2$ receptor) which is incubated with [3H]vasopressin in the presence or absence of the test compound. The $IC_{50}$ values (concentrations to inhibit [3H]vasopressin binding by 50%) for the various compounds (see Table III) are measures of their potencies and are inversely related to their affinities.

Vasopressin exerts its antidiuretic effects on the kidney through the stimulation of adenylate cyclase activity. Vasopressin stimulated adenylate cyclase in kidney medulla, therefore, is used as a functional assay to determine the potencies of the various test compounds as $V_2$-vasopressin antagonists. In this assay, the $IC_{50}$ values obtained for the various compounds (see Table III) are measures of their potencies to inhibit the vasopressin-stimulated conversion of ATP to cAMP by adenylate cyclase. This method was adapted from Seamon et al., *PNAS* 78: 3363-3367 (1981).

includes intravenous, intramuscular, intraperitoneal, subcutaneous and topical administration.

For oral use of an oxytocin or vasopressin antagonist of this invention, the selected compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When the compound of Formula I, its synthetic analogues and its minor related compounds or a salt thereof is used as an oxytocin or vasopressin antagonist in a human subject, the daily dosage will normally be determined by the prescribing physician. Moreover, the dosage will vary according to the age, weight and response of the individual patient, as well as the severity of the patient's symptoms. However, in most instances, an effective daily dosage will be in the range from about 1 mg to about 1500 mg and preferably 10 mg to 500 mg in a single or divided doses. On the other hand, it may be necessary to use dosages outside these limits in some cases.

TABLE IV

| Compound | | $IC_{50}$ Values[a] | | |
|---|---|---|---|---|
| | | [3H]-Arg[8]-Vasopressin Binding | | AVP-stimulated Ad. Cyclase |
| | | Liver ($V_1$) | Kidney ($V_2$) | Kidney ($V_2$) |
| Formula I | (n = 3-4) | 11.7 ± 1.7 μM[c] | 9.8 ± 1.7 μM[c] | 10.2 ± 1.1 μM |
| Component A | (n = 1) | 6.8 μM | 7.9 μM | 19 μM |
| Component B | (n = 4-5) | 67.3 ± 16.5 μM | 35.3 ± 6.1 μM | 62.7 ± 4.6 μM |
| Component C | (n = 3)[b] | 4.2 ± 0.4 μg/ml | 9.0 ± 0.6 μg/ml | 9.2 ± 2.1 μg/ml |
| | | (6 μM) | (13 μM) | (13 μM) |
| Component D | (n = 2)[b] | 20.6 μg/ml | 13.3 μg/ml | 14 μg/ml |
| | | (30 μM) | (19 μM) | (20 μM) |
| Component E | (n = 2) | 80 μM | 59 μM | 120 μM |
| Component F | (n = 2)[b] | >67 μg/ml | >67 μg/ml | >67 μg/ml |
| Component G | (n = 2-3)[b] | >67 μg/ml | >67 μg/ml | >67 μg/ml |

[a]Mean values with standard errors, as appropriate
[b]Exact MW not known: molar $IC_{50}$'s based on MW of 700
[c]Corresponds to Ki's of 1.9 μM (liver) and 4.0 μM (kidney): Ki = $IC_{50}$/(1 + c/Kd)

The ability of the compound of Formula I, its synthetic analogues and its minor related compounds to antagonize oxytocin and vasopressin makes these compounds useful as pharmaceutical agents. These compounds will be especially useful in the treatment and prevention of preterm labor or disease states wherein vasopressin may be involved, for example, congestive heart failure, hypertension, edema and hyponatremia.

The compound of Formula I, its synthetic analogues and its minor related compounds or a pharmaceutically acceptable salt thereof, can be administered to a human subject either alone, or preferably, in combination with pharmaceutically acceptable carriers or diluents, in a pharmaceutical composition, according to standard pharmaceutical practice. The compound can be administered orally or parenterally. Parenteral administration

What is claimed is:
1. Cyclic peptides having the formula:

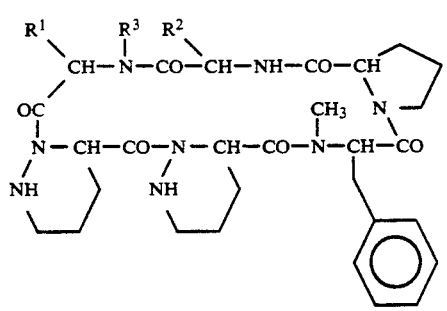

wherein

| Component | R¹ | R² | R³ |
|---|---|---|---|
| I | —CH(CH₃)CH₂(CH₃) | —CH₂C₆H₅ | —OH |
| Ia is | —CH(CH₃)CH₂(CH₃) | —CH₂C₆H₅ | —H |
| A is | —CH(CH₃)₂ | —CH₂C₆H₅ | —OH |
| B is | —CH₂CH(CH₃)₂ | —CH(CH₃)₂ | —OH |
| C is | —CH₂CH(CH₃)₂ | —CH₂C₆H₅ | —OH |
| D is | —CH₂CH(CH₃)₂ | —CH(CH₃)CH₂CH₃ | —OH | or the pharmaceutically acceptable salts thereof.

2. Cyclic peptides having the formula:

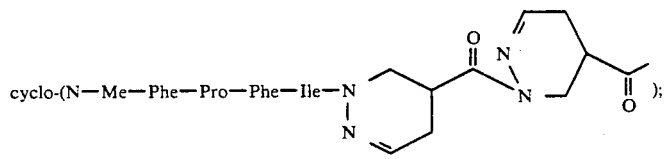

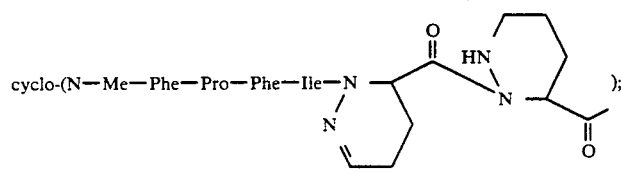

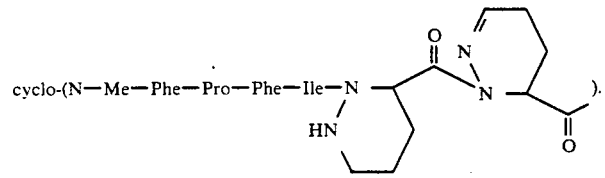

or the pharmaceutically acceptable salts thereof.

3. A method of antagonizing oxytocin in mammalian uterine tissue which comprises administering thereto a compound according to claim 1 or 2.

* * * * *